United States Patent
Connair (10) Patent No.: US 9,539,397 B2
(45) Date of Patent: *Jan. 10, 2017

(54) STEROID DELIVERY SYSTEM

(71) Applicant: Michael P. Connair, North Haven, CT (US)

(72) Inventor: Michael P. Connair, North Haven, CT (US)

(*) Notice: Subject to any disclaimer, the term of this patent is extended or adjusted under 35 U.S.C. 154(b) by 137 days.

This patent is subject to a terminal disclaimer.

(21) Appl. No.: 14/522,249

(22) Filed: Oct. 23, 2014

(65) Prior Publication Data

US 2015/0045773 A1    Feb. 12, 2015

Related U.S. Application Data

(62) Division of application No. 12/470,830, filed on May 22, 2009, now Pat. No. 8,894,608.

(51) Int. Cl.
*A61M 37/00* (2006.01)
*A61M 5/315* (2006.01)
(Continued)

(52) U.S. Cl.
CPC ......... *A61M 5/31596* (2013.01); *A61M 5/002* (2013.01); *A61M 5/19* (2013.01);
(Continued)

(58) Field of Classification Search
CPC ...... A61M 5/31596; A61M 5/19; A61M 5/32; A61M 2005/31598; A61M 2202/0007; A61M 2202/048
(Continued)

(56) References Cited

U.S. PATENT DOCUMENTS 3,527,216 A    9/1970 Snyder
3,946,732 A    3/1976 Hurscham
(Continued)

FOREIGN PATENT DOCUMENTS

EP    0882441 A2    12/1998

OTHER PUBLICATIONS

International Search Report and Written Opinion of the International Searching Authority; PCT/US2010/035919; Jul. 14, 2010; 11 pages.
(Continued)

*Primary Examiner* — Edelmira Bosques
(74) *Attorney, Agent, or Firm* — St Onge Steward Johnston and Reens LLC (57) ABSTRACT

A steroid delivery system including a mixing syringe having a first chamber and a second chamber and at least one hypodermic needle is provided. The first chamber of the mixing syringe contains a pre-measured volume of a local anesthetic and the second chamber contains a pre-measured volume of a corticosteroid. An improved mixing syringe and a method for treating pain using the steroid delivery system of the present invention is also provided herein. The improved syringe achieves mixing without the introduction or elimination of air and without puncturing or rupturing of a membrane, diaphragm or other material. The kit concept improves the speed of the procedure, sterility, accuracy of dosing, and immediate availability of disparate items to implement the procedure in a variety of medical practice settings.

20 Claims, 9 Drawing Sheets (51) Int. Cl.
*A61M 5/00* (2006.01)
*A61M 5/19* (2006.01)
*A61M 5/32* (2006.01)
*A61M 5/28* (2006.01)

(52) U.S. Cl.
CPC ............... *A61M 5/32* (2013.01); *A61M 5/284* (2013.01); *A61M 2005/31598* (2013.01); *A61M 2202/0007* (2013.01); *A61M 2202/048* (2013.01)

(58) Field of Classification Search
USPC .......................................................... 604/82
See application file for complete search history.

(56) References Cited

U.S. PATENT DOCUMENTS

| | | | |
|---|---|---|---|
| 4,116,240 A | 9/1978 | Guiney | |
| 4,171,698 A | 10/1979 | Genese | |
| 4,270,537 A | 6/1981 | Romaine | |
| 4,522,302 A | 6/1985 | Paikoff | |
| 5,067,948 A | 11/1991 | Haber et al. | |
| 5,300,030 A | 4/1994 | Crossman et al. | |
| 5,360,410 A | 11/1994 | Wacks | |
| 5,425,707 A | 6/1995 | Goldberg | |
| 5,487,732 A | 1/1996 | Jeffrey | |
| 5,807,323 A | 9/1998 | Kriesel et al. | |
| 6,033,386 A | 3/2000 | Novacek et al. | |
| 6,540,715 B1* | 4/2003 | Kuhn ...................... | A61K 9/08 366/162.4 |
| 7,100,771 B2 | 9/2006 | Massengale et al. | |
| 7,101,354 B2 | 9/2006 | Thorne, Jr. et al. | |
| 2005/0177100 A1 | 8/2005 | Harper et al. | |
| 2007/0066927 A1 | 3/2007 | Akelman et al. | |
| 2007/0225727 A1* | 9/2007 | Matsuhisa ............ | A61K 9/0048 606/107 |

OTHER PUBLICATIONS

Patent Examination Report No. 1 from Australia Application No. 2013251200 Issued: Feb. 2, 2015 3 pages.

* cited by examiner

STEROID DELIVERY SYSTEM

FIELD OF THE INVENTION

The present invention generally relates to pain management systems, and more specifically, a steroid delivery system for the treatment of localized musculoskeletal or neurogenic pain. Most specifically, the present invention relates to a prepackaged orthopedic steroid delivery system including an improved mixing syringe pre-filled with local anesthetic and corticosteroid, a variety of needles, local antiseptics, and ethyl chloride, if used.

BACKGROUND OF THE INVENTION

Steroid injections are often used to treat localized musculoskeletal or neurogenic pain. In practice, the corticosteroid is often mixed with a local anesthetic and injected into a patient's joint, tendon sheath, or adjacent to a painful ligament or inflamed nerve. The corticosteroid acts over several days to manage inflammation and pain, while the local anesthetic works immediately, but only temporarily. If the injection is properly placed, the local anesthetic will instantly numb the patient's pain, and the practitioner can be reasonably assured that the corticosteroid will be injected in the proper area to effectively manage pain. A successful local treatment of musculoskeletal or neurogenic pain improves the patient's function and decreases the need for systemic medications and even surgery, in some cases.

In the current state of the art, the preparation of such an injection requires a practitioner to gather a variety of supplies including the corticosteroid and anesthetic, a syringe and needles, and local anesthetic, among other things. The length of time it takes to prepare the injection can depend on the availability and accessibility of the supplies and the efficiency and organization of the medical office and staff. Lack of even one item, whether it is misplaced, out of stock, outdated, contaminated or in another area, can extend preparation time. The entire process can be very time consuming and can be a limiting factor in the number of such treatments a practitioner can administer in one day.

One example of a device that attempts to address these problems is disclosed in U.S. Pat. No. 7,100,771 B2 to Massengale et al. The Massengale patent relates to a pain management kit containing the primary medical supplies for performing a continuous nerve block procedure. The kit comprises sterile field supplies, local anesthetic supplies and continuous nerve block supplies in a single, sterile container. Inside the container, the supplies are organized within a series of compartmentalized trays which hold each of the included supplies. The particular anesthetic drug is omitted from the kit.

One disadvantage of this kit, however, is that the desired infusion drug and several other necessary supplies, such as nerve simulator and an infusion pump, are not contained within the kit. Therefore, the practitioner would still have to gather additional supplies, in addition to the kit, in order to perform the nerve block procedure. If any of these supplies are out of stock, misplaced, in another room, or in use by another practitioner, the procedure will be delayed.

Another factor which greatly affects the time to prepare an injection for pain management as described at the outset is that the practitioner must manually measure and mix the corticosteroid and anesthetic from separate vials immediately before use. This has several significant disadvantages. First, this can again add considerable time to the overall length of the procedure, depending on the dexterity and experience of the doctor. Even if all of the materials are within the practitioner's reach, he/she still must take the time to draw separate volumes of both the corticosteroid and anesthetic. Second, certain safety risks are associated with manually preparing the injection for each administration. Not only can human error play a role when manually measuring the two solutions, but also sterility is an issue when the vials of corticosteroid and anesthetic are reused to prepare several injections often by different practitioners at the same site. Third, the vials of corticosteroid and anesthetic have a limited shelf-life once they punctured, so if they are not completely used within the allotted time, they must be discarded, which can be costly. In fact, a practitioner that would not normally administer enough of these injections to avoid wasting opened vials of the pre-mixed corticosteroid or anesthetic may choose not to perform these types of procedures altogether.

However, in the current state of the art, corticosteroid premixed with local anesthetic is not readily commercially available. Many steroid preparations are suspensions of particles, which settle to the bottom of their glass vials within minutes of no motion. These particles can stick firmly to the glass vial and require vigorous shaking to re-suspend.

Furthermore, mixing syringes currently known in the field have the disadvantage of introducing air into the mixed solution. For example, in U.S. Pat. No. 7,101,354 to Thorne, Jr. et al., a small amount of air is contained in the chambers 120, 130 to aid in the creation of a negative pressure across the valved stopper 110. Any air within the chamber must be removed before injecting the mixed solution into a patient, which again can lengthen the time of a procedure.

Prior art mixing syringes also have the disadvantage of requiring the puncturing or rupturing of a membrane, diaphragm or other material separating the two injection solutions. When this rupturing or puncturing occurs, minute fragments of the separating material may be mixed into the injection. These materials may have an adverse effect when injected into the human body with the injection mixture.

What is desired, therefore, is a pre-packaged, sterile pain management kit which contains all of the instruments and supplies necessary to treat localized musculoskeletal or neurogenic pain. It is further desired to have a syringe containing pre-measured volumes of corticosteroid and local anesthetic in separate compartments that can be quickly mixed into a homogeneous chemical mixture immediately prior to use, without rupturing or puncturing of a separating material and without introducing air into the mixture.

SUMMARY OF THE INVENTION

Accordingly, it is an object of the present invention to provide a sterile steroid delivery system which contains all of the instruments and supplies necessary for a pain management treatment.

It is a further object of the present invention to provide a method for treating pain using the corticosteroid delivery system of the present invention.

It is still a further object of the present invention to provide an improved mixing syringe for mixing corticosteroid and local anesthetic immediately prior to use for pain management in conjunction with the corticosteroid delivery system of the present invention.

These and other objectives are achieved by providing a steroid delivery system comprising a mixing syringe having a first chamber and a second chamber, the first chamber containing a pre-measured volume of a local anesthetic and the second chamber containing a pre-measured volume of a corticosteroid, and at least one hypodermic needle. The mixing syringe and at least one needle may be sealed within said sterile package. The local anesthetic may be chosen from the group consisting of: lidocaine, xylocaine, ropivacaine, marcaine, or similar. Further, the corticosteroid may be chosen from the group consisting of betamethasone, triamcinolone, and methylprednisolone. In other embodiments, the steroid delivery system further comprises at least one 22 gauge hypodermic needle, at least one 25 gauge hypodermic needle, a local surface anesthetic, and a local antiseptic. In yet further embodiments of the present invention, the volume of local anesthetic varies based on the intended treatment area and desired effect and the volume of corticosteroid varies based on the intended treatment area and desired effect. Moreover, the ratio of the volume of local anesthetic to the volume of corticosteroid may vary based on the intended treatment area and desired effect.

Other objects of the present invention are achieved by provision of a method for treating pain and inflammation comprising the steps of: providing a steroid delivery system having a mixing syringe having a first chamber and a second chamber and at least one hypodermic needle; combining said pre-measured volume of local anesthetic and pre-measured volume of corticosteroid within the mixing syringe into an injection mixture prior to injection, and injecting said injection mixture into an intended treatment area. The first chamber of the syringe contains a pre-measured volume of local anesthetic and the second chamber contains a pre-measured volume of corticosteroid. In some embodiments, the method further comprises the step of choosing the volume of local anesthetic based on the intended treatment area and desired effect. In other embodiments, the method further comprises the step of choosing the volume of corticosteroid based on the intended treatment area and desired effect. In further embodiments, the method further comprises the step of choosing the ratio of the volume of local anesthetic to the volume of corticosteroid based on the intended treatment area and desired effect.

Still other objects of the present invention are achieved by provision of a mixing syringe comprising a first chamber adapted for containing an injectable material, a second chamber in axial alignment with the first chamber and adapted for containing an injectable material, a cannula having an end open to said first chamber and having a lateral opening spaced apart from the end thereof, a mixing assembly disposed between the first and second chambers, said mixing assembly supporting the cannula for axial movement and covering the lateral opening when the cannula is in an inoperative position, a retracting element attached to the cannula, axial movement of the retracting element causing corresponding axial movement of the cannula such that the cannula is retracted from the inoperative position to an operative position where the lateral opening lies within the second chamber, so that the second chamber is in fluid communication with the first chamber.

In some embodiments, the mixing assembly comprises a first sealing element slidably disposed between the first chamber and second chamber and a second sealing element at least partially disposed within the first chamber and second chamber. The first may have sealing element has an axial hole therethrough for slidably receiving the second sealing element therein. In further embodiments, the syringe further comprises a hollow barrel having an inner surface, an open proximal end and a distal end, the barrel distal end being adapted to receive a hypodermic needle. The first chamber of the syringe is defined by the barrel inner surface between the barrel proximal end and the mixing assembly.

In other embodiments, the retracing element comprises a flange. In yet other embodiments, the retracting element comprises a lever, hingedly affixed to the cannula.

Other objects of the invention and its particular features and advantages will become more apparent from consideration of the following drawings and accompanying detailed description.

DETAILED DESCRIPTION OF THE INVENTION

Figure 1:
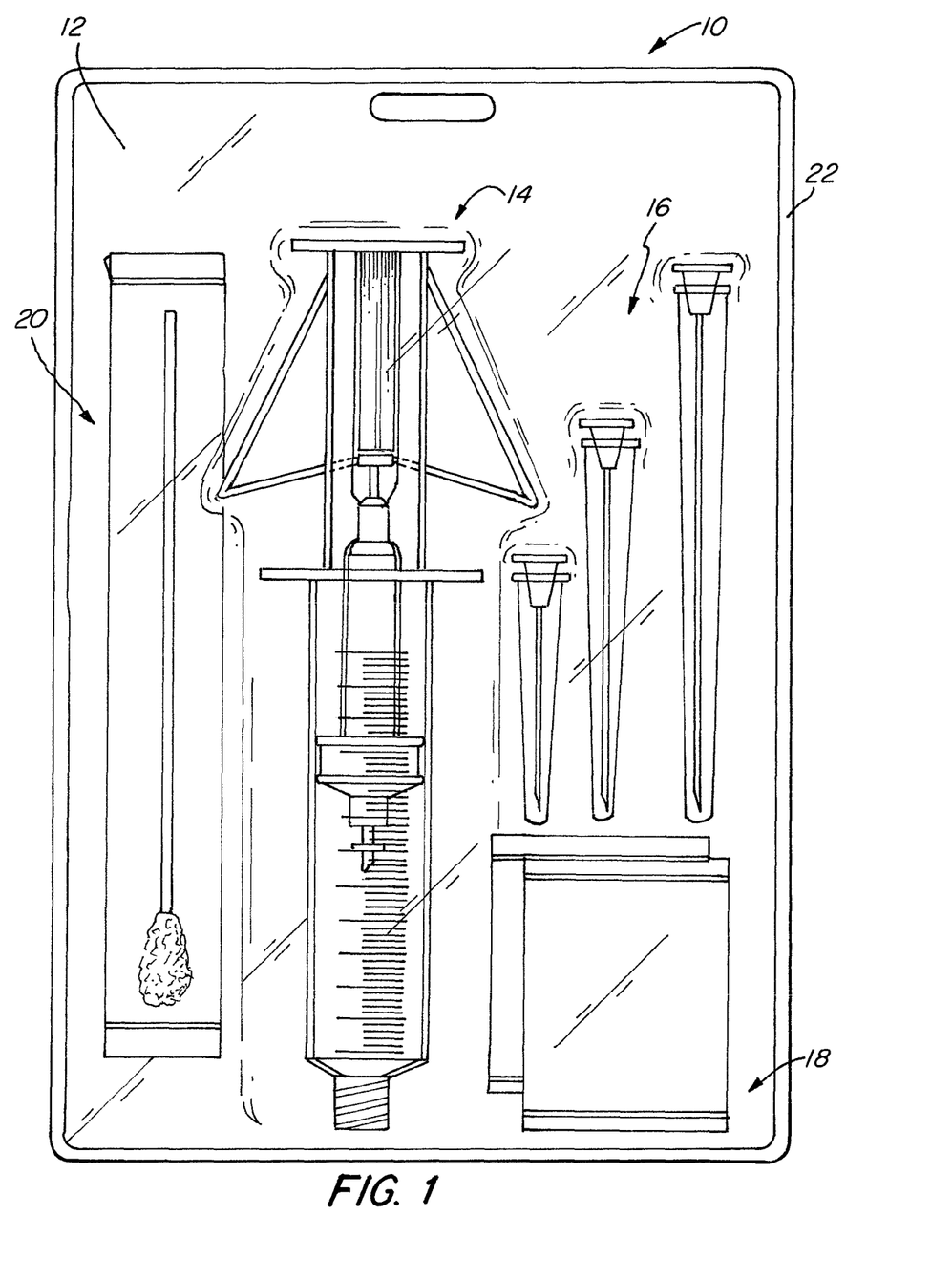
FIG. 1 is a top view of one embodiment of the steroid delivery system of the present invention.
Figure 2:
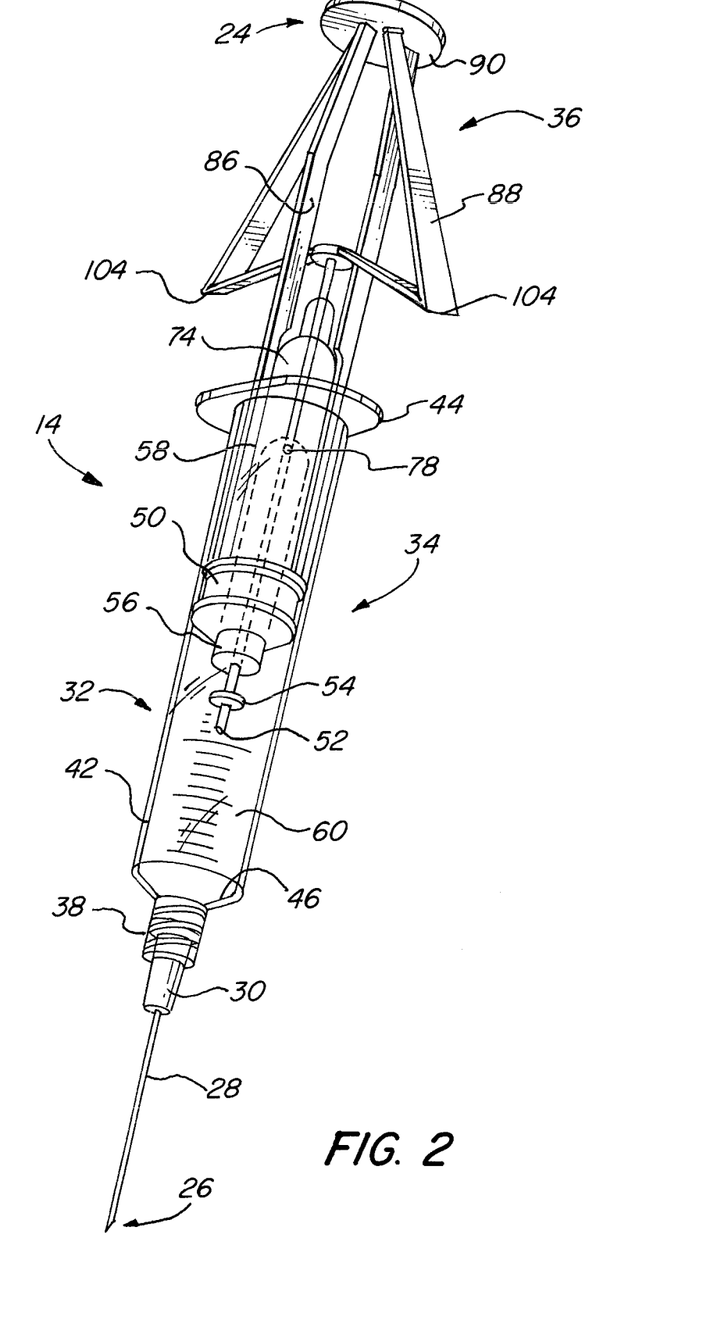
FIG. 2 is a perspective view of one embodiment of the improved mixing syringe for use in the steroid delivery system of the present invention.

One embodiment of the steroid delivery system 10 of the present invention is shown in FIG. 1. The steroid delivery system 10 consists of a kit 12 containing all of the medical supplies necessary to administer a corticosteroid and anesthetic treatment including, but not limited to, an improved mixing syringe 14 prefilled with a volume of local anesthetic and corticosteroid, a variety of hypodermic needles 16, local antiseptic wipes (e.g. povidine, isopropyl alcohol) 18, an antiseptic swab 20 and a local surface anesthetic (not shown), such as ethyl chloride, if used. All of the desired items for administering the treatment are contained within a sterile package 22 so that the items may be removed and immediately used. As stated above, the time it currently takes to administer this treatment is highly dependent on the availability and accessibility of all of the necessary supplies. By bundling all of the supplies into one kit, the preparation time will be greatly reduced and increase the likelihood that such an injection can be achieved on short notice.

Furthermore, the prepackaged kit 12 can be produced in a variety of corticosteroid to anesthetic ratios and quantities, for the treatment of pain in different areas of the body, such as a joint, a tendon sheath, a ligament, or a nerve. One having skill in the art is familiar with the particular volumes and strengths of both the anesthetic and corticosteroid that are safe and effective for the relief of pain and inflammation in certain areas of the body. In addition, by providing a variety of hypodermic needles 16 of different lengths and gauges, one kit 12 may be used to treat a variety of areas. For example, at least one 25 gauge needle, and at least one 22 gauge needle may be provided in one kit 12. Moreover, the needles can be provided in varying lengths, such a spinal-length needle.

Referring now to FIGS. 2 and 3A-3C, the improved mixing syringe 14 for use in the corticosteroid delivery system 10 of the present invention, having a proximal end 24 and a distal end 26, comprises a hypodermic needle 28 having a neck 30, a barrel 32, a mixing assembly 34 and a retracting assembly 36. Hypodermic needle 28 would be provided separately of the syringe 14 within the sterile kit 12 and would be connected by the practitioner immediately before administration. Barrel 32 is a conventional syringe barrel known in the art, having a nozzle 38 for accepting a hypodermic needle, a fluid dispensing orifice 40, a hollow cylinder 42 and a grip 44. Distal end 46 of barrel 32 has is contoured to maximize effluent flow and to minimize fluid retained in barrel 32 as a plunger or stopper is displaced to abut the distal end. Prior to use and during the mixing phase, orifice 40 is closed and sealed by a removable cap 48.

Mixing assembly 34 comprises stopper 50, cannula 52, flange projection 54, elongate plug 56 and vial 58. Slidably disposed within hollow cylinder 42 of barrel 32 between distal end 46 and grip 44, stopper 50 defines a first chamber 60 for containing a first injectable material. Stopper 50 is sufficiently close fitting with hollow cylinder 42 to be fluid tight and has a generally convex distal end 62 that corresponds to distal end 46 of barrel 32. Vial 58 is received within proximal portion 66 of channel 64 of stopper 50 and rests on ledge 68. Again, vial 58 is sufficiently close fitting with the proximal portion 66 of channel 64 to be fluid tight. While not necessary, vial 58 may be affixed within channel 64 of stopper 50 with an adhesive.

Elongate plug 56 is slidably disposed within distal portion 70 of stopper 50. The diameter of distal portion 70 is approximately the same as the diameter of inner surface 72 of vial 58. Thus, plug 56 is fluid tight with both the internal surface 72 of vial 58 and the distal portion 70 of stopper 50. Cannula 52, having a lateral opening 78 and a distal opening 80 and a solid segment 81 proximal of the lateral opening 78, is slidably received within internal passage 76 of plug 56. Cannula 52 is hollow from distal opening 80 to the solid segment 81. Thus, with cannula 52 received in passage 76, plug 56 defines a second chamber 74 within vial 58 for containing a second injectable material.

Figures 3A, 3B:
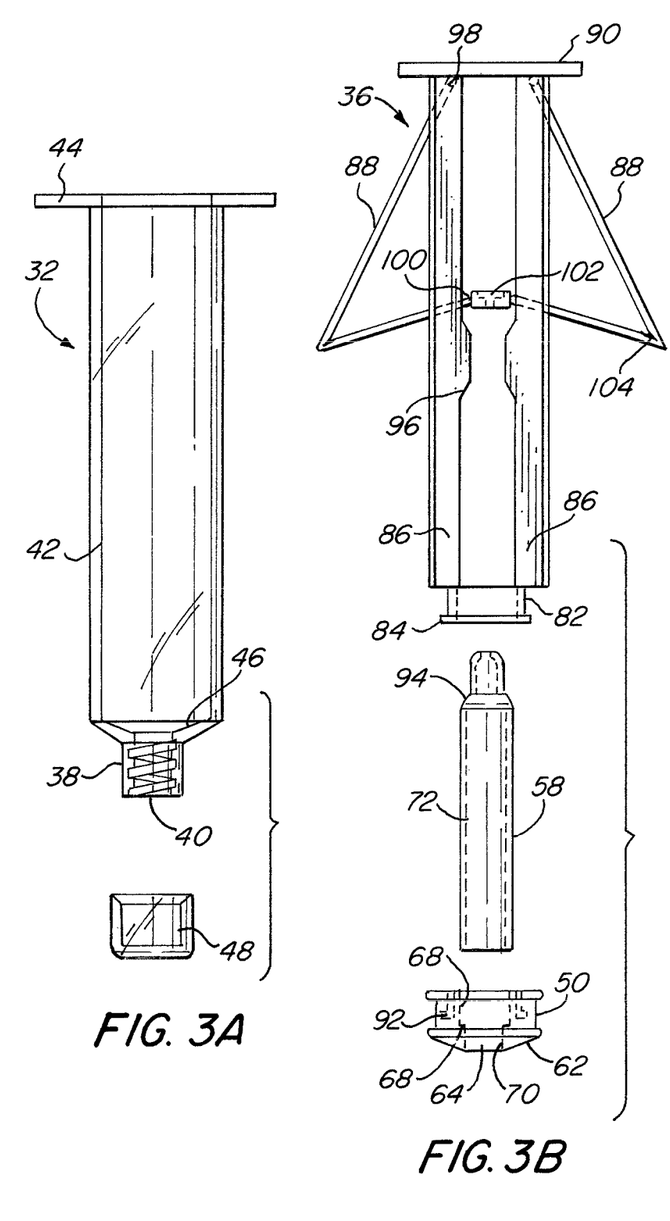
FIG. 3a is a side view of one embodiment of a syringe barrel for use in the steroid delivery system of the present invention.
FIG. 3b is a side view of the stopper, vial, and retracting assembly for use in the steroid delivery system of the present invention.
Figure 3C:
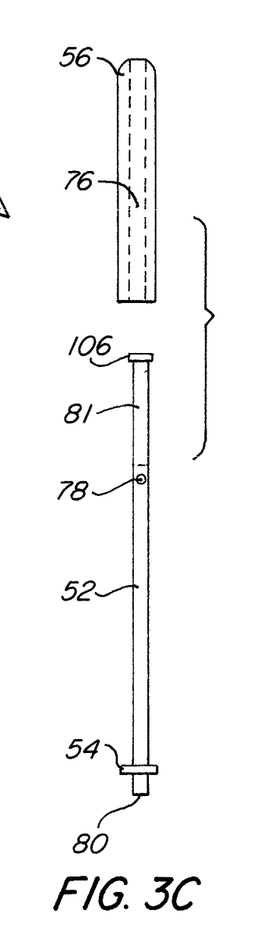
FIG. 3c is a side view of the cannula and for use in the steroid delivery system of the present invention.

Referencing FIG. 3B, retracting assembly 36 comprises a connecting portion 82 having a lip 84, struts 86, lever arms 88 and a plunger 90. Together, connecting portion 82, struts 86, plunger 90, and stopper 50 are similar in function and structure to a plunger stem of basic syringes known in the art. When assembled, lip 84 of connecting portion 82 is inserted into groove 92 of stopper 50 and shoulder 94 of vial 58 rests against ridge 96 of struts 86.

Figure 4:
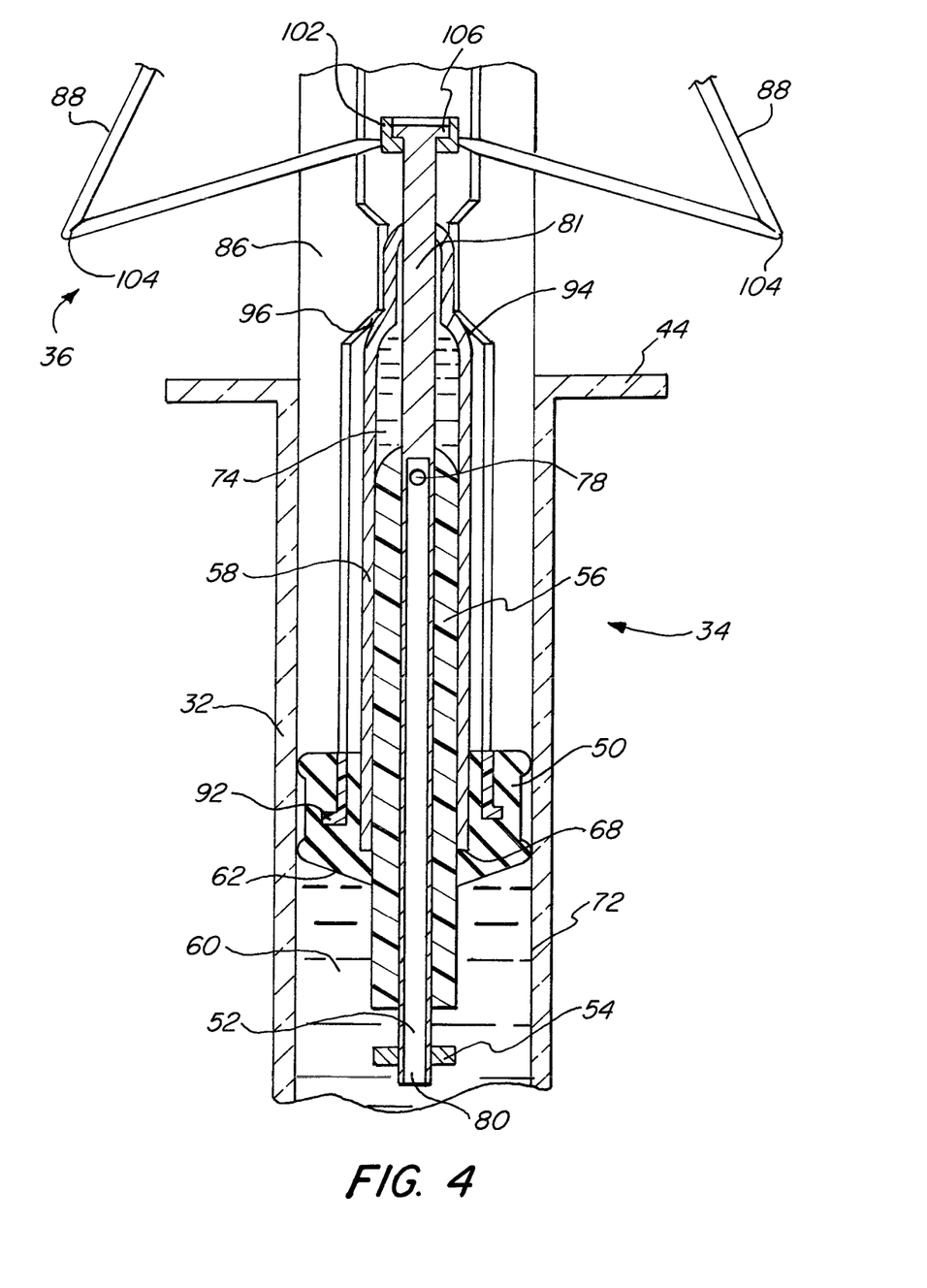
FIG. 4 is a detailed partial side view of one embodiment of the improved mixing syringe for use in the steroid delivery system of the present invention.

Lever arms 88 are hingedly affixed at a proximal end 98 to plunger 90 and at a distal end 100 to disk 102. Head 106 of cannula 52 is engaged with disk 102. Preferably, lever arms 88 are formed as one continuous piece and hinge at elbow 104. However, each lever arm 88 may be formed of two separate pieces of plastic and hingedly connected at elbow 104. To allow lever arms 88 to hinge at elbows 104 and the connections at proximal 98 and distal 100 ends, arms 88 are preferably formed of a molded plastic that is robust, yet has some flex to it, such as a low density polyethylene (LDPE), high density polyethylene (HDPE), or polypropylene (PP). Moreover, lever arms may be integrally formed with plunger 90 and disk 102. As is depicted in FIG. 3B, elbows 104 are positioned slightly lower (more distal) than disk 102, the utility of which will be described below. A detailed view of the assembled mixing assembly 34 and its connection to the retracting assembly 36 is shown in FIG. 4.

Figure 5:
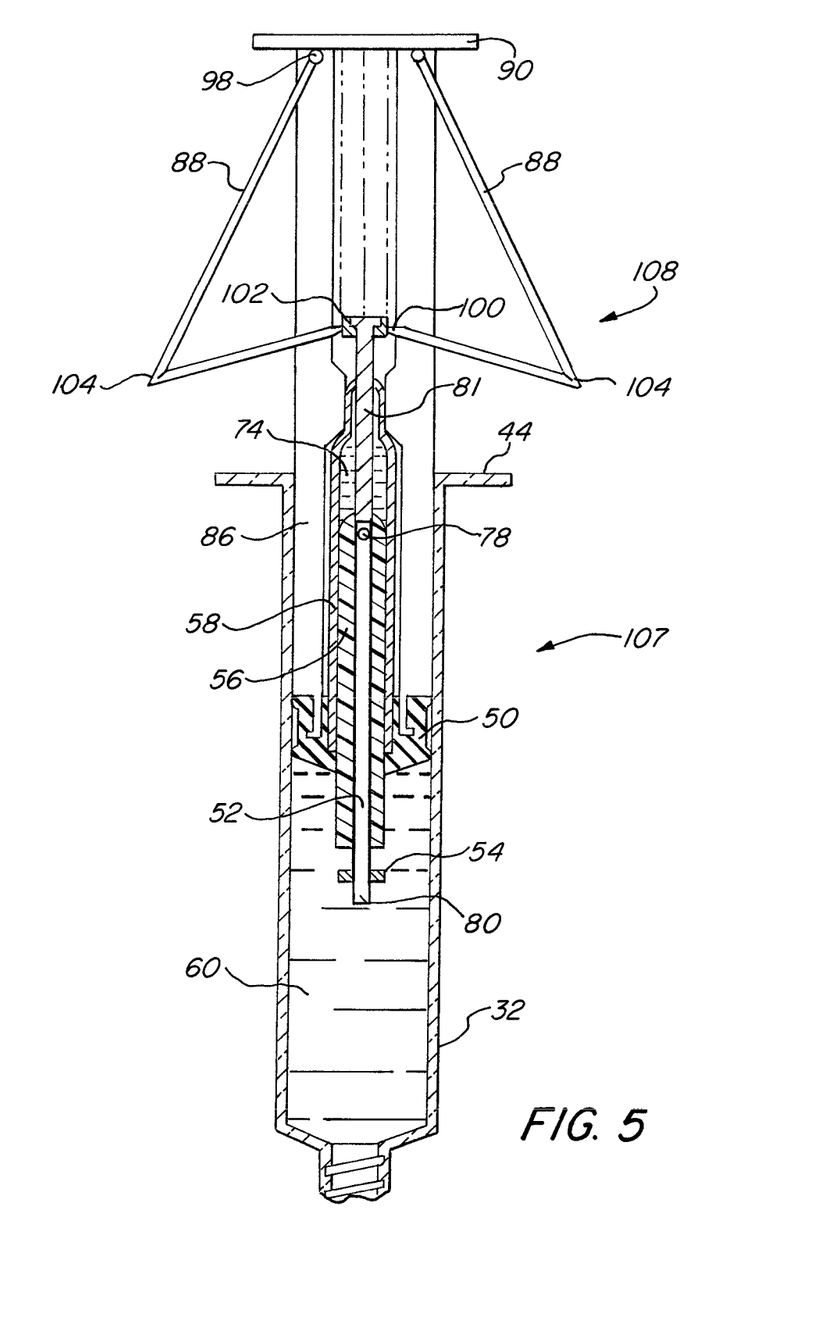
FIG. 5 is a side view of one embodiment of the improved mixing syringe for use in the steroid delivery system of the present invention.

FIG. 5 depicts mixing syringe 14 in an inoperative position 107 in which lateral opening 78 of cannula 52 is sealed by plug 56. Thus, while distal opening 80 of cannula 52 is open to first chamber 60, second chamber 74 is not in communication with first chamber 60. In this inoperative position 107, plug 56 extends partially into first chamber 60 and flange projection 54 is spaced apart both from distal end of cannula 52 and plug 56. Further, lever arms 88 are in an open position 108. This is how mixing syringe 14 would be provided in the sterile kit 12.

Figure 6:
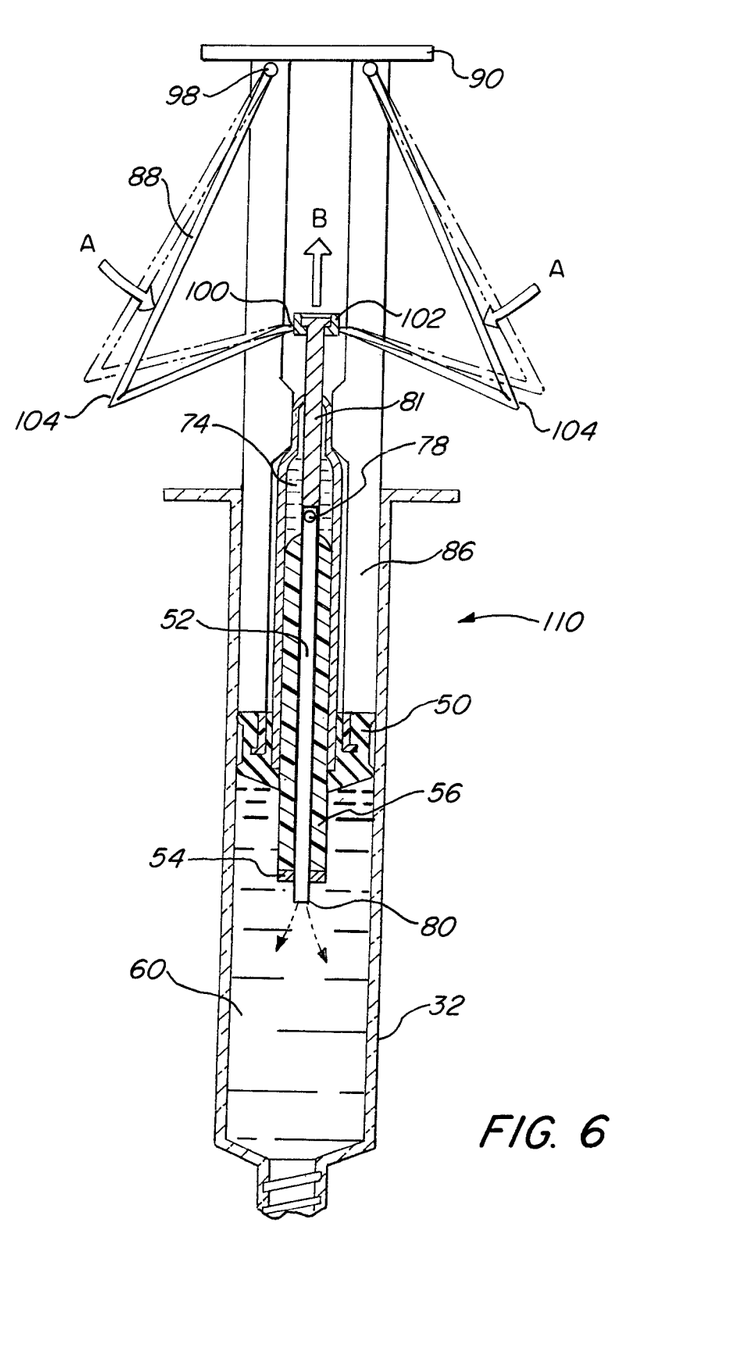
FIG. 6 is a side view of one embodiment of the improved mixing syringe for use in the steroid delivery system of the present invention.

As stated above, the improved mixing syringe 14 contains separate, pre-measured volumes of two injectable materials, preferably a corticosteroid and a local anesthetic. Additionally, the syringe is designed so that the two component medications can be quickly combined into a homogeneous chemical mixture just prior to use. In operation, as shown in FIG. 6, to mix the injectable materials in first chamber 60 and second chamber 74, a practitioner squeezes lever arms 88 in the direction of arrow A. This squeezing is a simple motion and will be familiar to practitioners in the art and intuitive to less frequent practitioners. Due to the hinged connections at proximal end 98, distal end 100, and elbows 104, and the orientation of disk 102 with respect to elbows 104 causes disk 102 to move proximally in the direction of arrow B. As cannula 52 is engaged with disk 102, it is also drawn in the direction of arrow B. Mixing syringe 14 is in an operative position 110 when lateral opening 78 lies fully within second chamber 74, causing second chamber 74 to be in fluid communication with first chamber 60 and allowing the respective injectable materials contained therein to mix. Further, as cannula 52 was drawn in the direction of arrow B, flange projection 54 was moved into abutment with plug 56.

As the user continues to squeeze lever arms 88 in the direction of arrow A, cannula 52 continues to be drawn in the direction of arrow B. Now, because flange projection 54 was moved into abutment with plug 56, plug 56 is also drawn proximally in the direction of arrow B and into second chamber 74. Plug 56 is drawn into chamber 74 until its proximal end abuts the inner surface of shoulder 94 of the vial 58, fully expelling substantially all of the injectable material contained in second chamber 74 into first chamber 60 through opening 80. The injectable mixture is now fully contained within first chamber 60. Notably, the total volume of the first 60 plus the second 74 chambers remains constant from the beginning and throughout the mixing process. Moreover, no air is introduced into either of the chambers and no separating material is ruptured or punctured in the mixing process.

Figure 7:
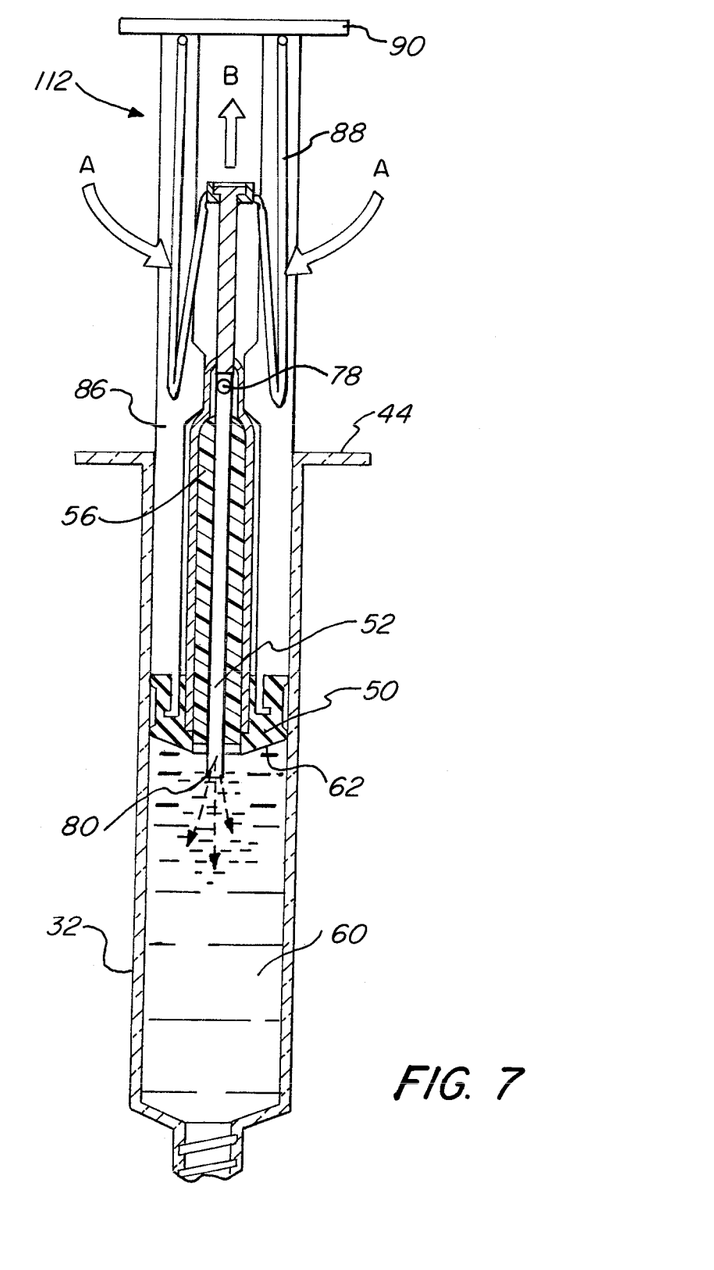
FIG. 7 is a side view of one embodiment of the improved mixing syringe for use in the steroid delivery system of the present invention.
Figure 8:
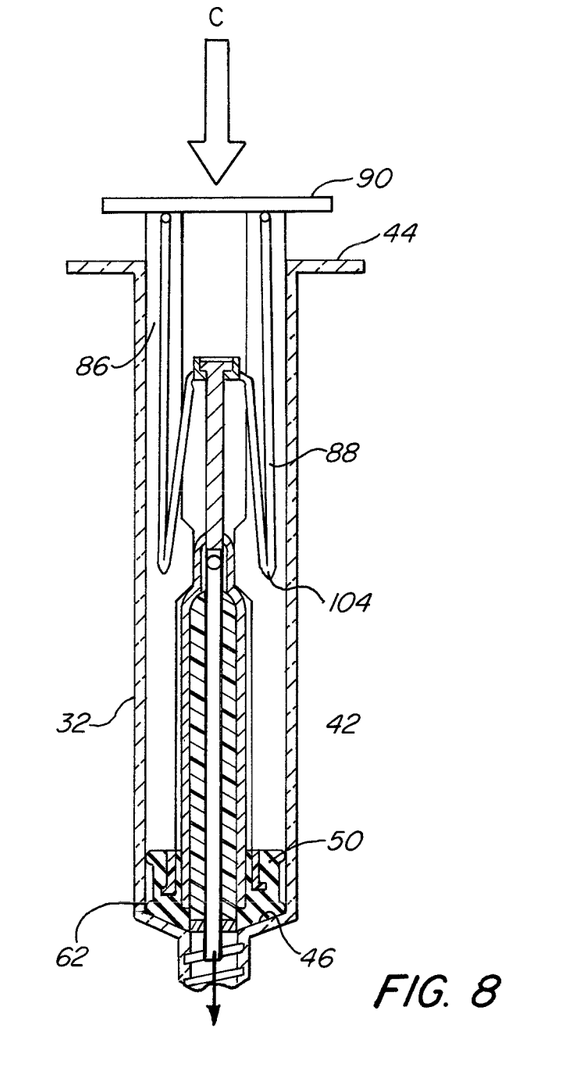
FIG. 8 is a side view of one embodiment of the improved mixing syringe for use in the steroid delivery system of the present invention.

After the injectable materials are mixed, the user would then connect a hypodermic needle 28 to nozzle 38 of syringe barrel 32 in preparation for administration. As can be seen in FIG. 7, when lever arms 88 are in a closed position 112, they are folded in, hinged at elbows 104, and lie completely within the profile of the struts 86. Therefore, when plunger 90 is depressed in the direction of arrow C, as shown in FIG. 8, the struts 86 and arms 88 fit within hollow cylinder 42 of barrel 32. The injectable mixture is then expelled out of barrel 32 through fluid dispensing orifice 40 (and through needle 28) as plunger 90 is depressed. All of the fluid is expelled once convex distal end 62 of stopper 50 abuts distal end 46 of barrel 32.

The mixing syringe 14 may be used in conjunction with the steroid delivery system of the present invention, for the purpose of treating musculoskeletal or neurogenic pain. In this embodiment, the first injectable material contained within the first chamber 60 is preferably a local anesthetic, which may be lidocaine, xylocaine, ropivacaine, or marcaine. The second injectable material contained within the second chamber 74 is preferably a corticosteroid, which may contain particles settled in the suspension. The corticosteroid may be betamethasone, triamcinolone, or methylprednisolone, or others. By placing the corticosteroid in the second chamber, any particles that have settled to the bottom of the chamber will be dispersed throughout the solution when the local anesthetic from the first chamber is introduced. The corticosteroid and anesthetic may be reversed when there is no particle suspension.

The mixing syringe 14 of the present invention may also be used in any instance where it is desirable to administer two injectable solutions at one time, but where the two solutions must be kept separate prior to injection. Therefore, the first and second chambers may be pre-filled with any desired injectable solutions, particulate suspensions, powders, etc.

Figure 9:
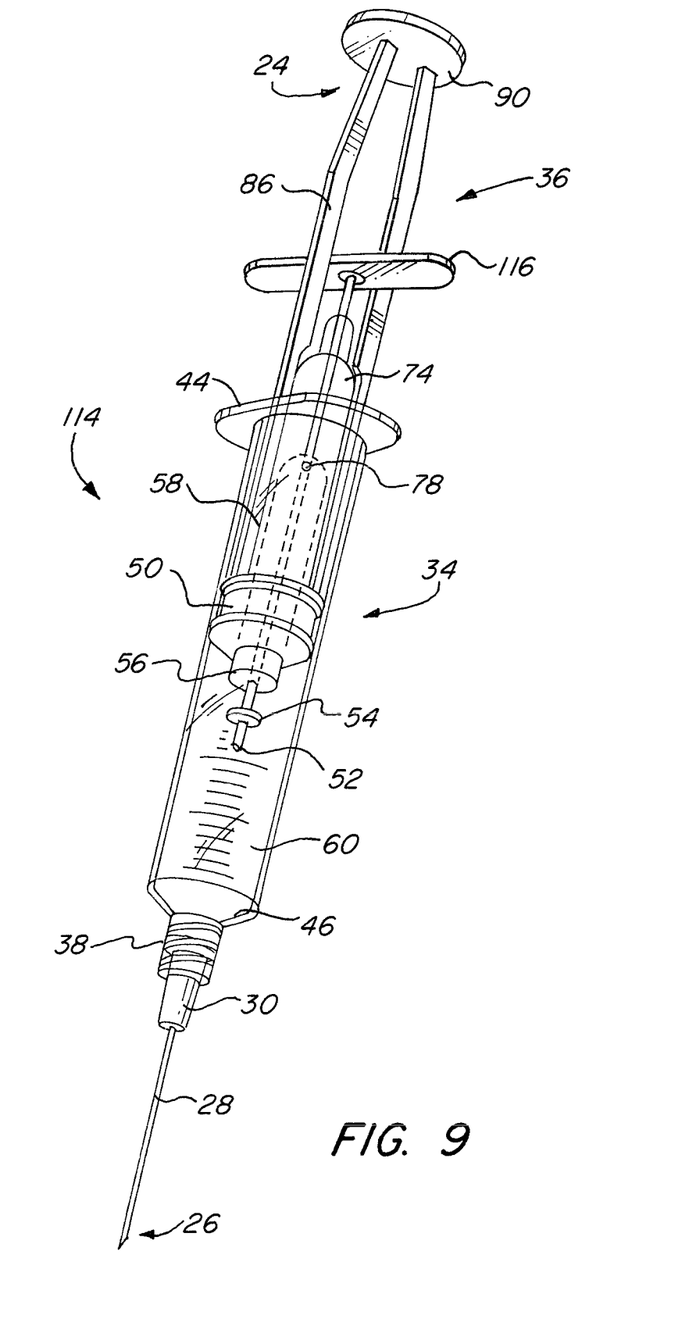
FIG. 9 is a perspective view of one embodiment of the improved mixing syringe for use in the steroid delivery system of the present invention.

An alternative embodiment of the improved mixing syringe 114 for use in the steroid delivery system of the present invention is shown in FIG. 9. Like elements are labeled the same. This embodiment of syringe 114 functions the same as syringe 14, except that the lever arms 88 and disk 102 of the retracting assembly 36 are replaced with a flange 116, which is connected to the proximal end of the cannula 52. In operation, a user merely grasps flange 116 and pulls it in the proximal direction to move syringe 114 from an inoperative position 107 to an operative position 110. Other embodiments of retracting assembly 36, including a threaded mechanism wherein a user would twist the retracting assembly and cause it to draw the cannula proximally, are also contemplated.

It should be understood that the foregoing is illustrative and not limiting, and that obvious modifications may be made by those skilled in the art without departing from the spirit of the invention. Accordingly, reference should be made primarily to the accompanying claims, rather than the foregoing specification and relative dimensions shown and described therein, to determine the scope of the invention.

What is claimed is:

1. A steroid delivery system comprising:
a mixing syringe having a first chamber and a second chamber,
said first chamber containing a pre-measured volume of a first injectable material, said second chamber containing a pre-measured volume of a second injectable material, and a hypodermic needle, wherein said mixing syringe further includes: a mixing assembly comprising an elongated plug disposed between said first and said second chambers, said second chamber in axial alignment with said first chamber, a cannula having an end and a lateral opening spaced apart from the end thereof, said cannula end being open to said first chamber in an inoperative position, and a retracting element attached to said cannula; wherein said elongated plug of said mixing assembly has an internal passage for slidably receiving said cannula and supporting said cannula for axial movement, said elongated plug completely covering said lateral opening of said cannula when said cannula is in an inoperative position, such that said first chamber is not in fluid communication with said second chamber; and wherein axial movement in the proximal direction of said retracting element causes corresponding axial movement of said cannula such that said cannula is retracted from said inoperative position to an operative position where said lateral opening lies within said second chamber, such that said second chamber is in fluid communication with said first chamber.

2. The steroid delivery system of claim 1, wherein one of said first and second injectable materials is a corticosteroid.

3. The steroid delivery system of claim 1, further comprising a sterile package, wherein said mixing syringe and at least one needle are sealed within said sterile package.

4. The steroid delivery system of claim 2, wherein said corticosteroid is chosen from the group consisting of betamethasone, triamcinolone, and methylprednisolone.

5. The steroid delivery system of claim 2, wherein the other of the first and second injectable materials is a local anesthetic.

6. The steroid delivery system of claim 5, wherein said local anesthetic is chosen from the group consisting of: lidocaine, ropivacaine, xylocaine and marcaine.

7. The steroid delivery system of claim 5, wherein the ratio of the volume of said local anesthetic to the volume of said corticosteroid varies based on the intended treatment area and desired effect.

8. The steroid delivery system of claim 1, wherein said second injectable material is in the form of a particulate suspension.

9. The steroid delivery system of claim 1, wherein said hypodermic needle is selected from the group consisting of a 22 gauge hypodermic needle, a 25 gauge hypodermic needle, and a combination thereof.

10. The steroid delivery system of claim 1 further comprising a local surface anesthetic.

11. The steroid delivery system of claim 10, wherein said local surface anesthetic is ethyl chloride.

12. The steroid delivery system of claim 1 further comprising a local antiseptic.

13. The steroid delivery system of claim 12, wherein said local antiseptic is chosen from the group consisting of isopropyl alcohol and povidine.

14. A method for treating pain comprising:
providing the steroid delivery system of claim 1,
combining said first injectable material and said second injectable material within the mixing syringe into an injection mixture;
attaching said hypodermic needle to said mixing syringe; and
injecting said injection mixture into an intended treatment area through said hypodermic needle.

15. The method for treating pain of claim 14 further comprising the step of choosing said volume of local anesthetic based on the intended treatment area and desired effect.

16. The method for treating pain of claim 14 further comprising the step of choosing said volume of corticosteroid based on the intended treatment area and desired effect.

17. The method for treating pain of claim 14 further comprising the step of choosing the ratio of the volume of local anesthetic to the volume of corticosteroid based on the intended treatment area and desired effect.

18. The method for treating pain of claim 14, wherein said intended treatment area is chosen from the group consisting of a joint, a tendon sheath, a ligament and a nerve.

19. The method for treating pain of claim 14, wherein said combining step is performed without the introduction or elimination of air from the mixing syringe.

20. The method for treating pain of claim 14 wherein said combining step is performed without puncturing or rupturing of a membrane, diaphragm or other material.

\* \* \* \* \*